United States Patent [19]

VandenBerg

[11] Patent Number: Plant 7,603

[45] Date of Patent: Jul. 23, 1991

[54] CHRYSANTHEMUM PLANT NAMED WHITE CARICIA

[75] Inventor: Cornelis P. VandenBerg, Salinas, Calif.

[73] Assignee: Yoder Brothers, Inc., Barberton, Ohio

[21] Appl. No.: 436,029

[22] Filed: Nov. 14, 1989

[51] Int. Cl.[5] ..... A01H 5/00

[52] U.S. Cl. ..... Plt./74

[58] Field of Search ..... Plt./74

[56] References Cited

U.S. PATENT DOCUMENTS

P.P. 6,902 7/1989 VandenBerg ..... Plt. 74

4,616,099 10/1986 Sparkes ..... 47/58 X

OTHER PUBLICATIONS

Searle, S. A. et al., "Use of Gamma and X-rays"; Appendix I: Varieties *Chrysanthemums the Year Round,* Blandford Press, London, 1968, pp. 27–29; 320–327.

Gosling, S. G., "Appendix II: Sporting and Irradiation" *The Chrysanthemum Manual* Nat. Chrysanth. Soc., London, 1979, pp. 329–337.

*Primary Examiner*—James R. Feyrer

*Attorney, Agent, or Firm*—Foley & Lardner

[57] ABSTRACT

A Chrysanthemum plant named White Caricia particularly characterized by its flat capitulum form; anemone capitulum type; white ray floret color; diameter across face of capitulum of up to 7 cm at maturity; diameter of anemone cushion up to 22 mm; uniform eight week photoperiodic flowering response to short days; peduncle length ranging from 8 to 18 cm on open, terminal sprays; medium plant height when grown as a single stem spray cut mum; and excellent tolerance to low temperatures for bud initiation and flower development.

1 Drawing Sheet

The present invention comprises a new and distinct cultivar of Chrysanthemum, botanically known as *Dendranthema grandiflora,* and referred to by the cultivar name White Caricia.

White Caricia, identified as 84-567A01, is a product of a mutation induction program which had the objective of creating new Chrysanthemum cultivars that would expand the color range of an existing cultivar while retaining all other traits.

White Caricia was discovered and selected by Cornelis P. VandenBerg on Nov. 17, 1987 in a controlled environment in Salinas, Calif. as one flowering plant within a flowering block established as rooted cuttings from stock plants which had been exposed as unrooted cuttings to an X-ray source of 1500 rads. The irradiated parent was the cultivar identified as Caricia, disclosed in plant patent application Ser. No. 187,654, now U.S. Plant Pat. No. 6,902.

The first act of asexual reproduction of White Caricia was accomplished when vegetative cuttings were taken from the initial selection in January 1988 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for White Caricia are firmly fixed and are retained through successive generations of asexual reproduction.

White Caricia has not been observed under all possible environmental conditions. The phenotype may vary significantly with variations in environment such as temperature, light intensity and daylength.

The following observations, measurements and comparisons describe plants grown in Salinas, Calif. under greenhouse conditions which approximate those generally used in commercial greenhouse practice. The low temperature tolerance of the new variety as noted below was determined in repeated flowerings in Bogota, Colombia.

The following traits have been repeatedly observed and are determined to be basic characteristics of White Caricia, which, in combination, distinguish this Chrysanthemum as a new and distinct cultivar:

1. Flat capitulum form.
2. Anemone capitulum type.
3. White ray floret color.
4. Diameter across face of capitulum up to 7 cm at maturity, with diameter of anemone cushion up to 22 mm.
5. Uniform eight week photoperiodic flowering response to short days.
6. Penduncle length ranging from 8 to 18 cm on open, terminal sprays.
7. Medium plant height, requiring two long day weeks prior to short days to attain a flowered plant height of 90 to 100 cm for year-round flowerings.
8. Excellent tolerance to low temperatures for bud initiation and flower development.

The accompanying photographic drawing shows typical inflorescence and leaf characteristics of White Caricia, with the colors being as nearly true as possible with illustrations of this type. The color photograph is a perspective view of White Caricia grown as a single stem cut spray mum.

Of the commercial cultivars known to the inventor, the most similar in comparison to White Caricia are the parent cultivar Caricia, and the induced mutation Pink Caricia, created through the same mutation induction program as White Caricia, and disclosed in applicant's pending application Ser. No. 07/435,821, filed simultaneously with the present application. All traits of White Caricia are similar to those of Caricia and Pink Caricia, except the color of the ray florets. The color of the ray florets of White Caricia is white, compared to the very soft pink ray florets of Caricia. The ray florets of Pink Caricia are a substantially darker shade of pink compared to the ray florets of Caricia.

In the following description color references are made to the Royal Horticultural Society Colour Chart. The color values were determined on plant material grown as a single stem cut spray mum in Salinas, Calif. on July 14, 1989.

Classification:

*Botanical.*—*Dendranthema grandiflora* cv White Caricia.

*Commercial.*—Anemone cut spray mum.

INFLORESCENCE

A. Capitulum:

*Form.*—Flat.

*Type.*—Anemone.

*Diameter across face.*—Up to 7 cm at maturity.

*Diameter of anemone cushion.*—Up to 22 mm.

B. Corolla of ray florets:

*Color (general tonality from a distance of three meters).*—White.

*Color (upper surface).*—Closest to 155D.

*Color (under surface).*—Closest to 155D.

*Shape.*—Flat, oblong.

C. Corolla of disc florets:

*Color (mature).*—155C, with tips of anemone disc florets 6A to 6B.

*Color (immature).*—Closest to 144B to 145A.

D. Reproductive organs:

*Androecium.*—Present on disc florets only; scant pollen.

*Gynoecium.*—Present on both ray and disc florets.

PLANT

A. General appearance:

*Height.*—Medium; 90 to 100 cm as a single stem cut mum with two long day weeks prior to short days.

B. Foliage:

*Color (upper surface).*—147A.

*Color (under surface).*—147B.

*Shape.*—Lobed and slightly serrated.

I claim:

1. A new and distinct Chrysanthemum plant named White Caricia, as described and illustrated.

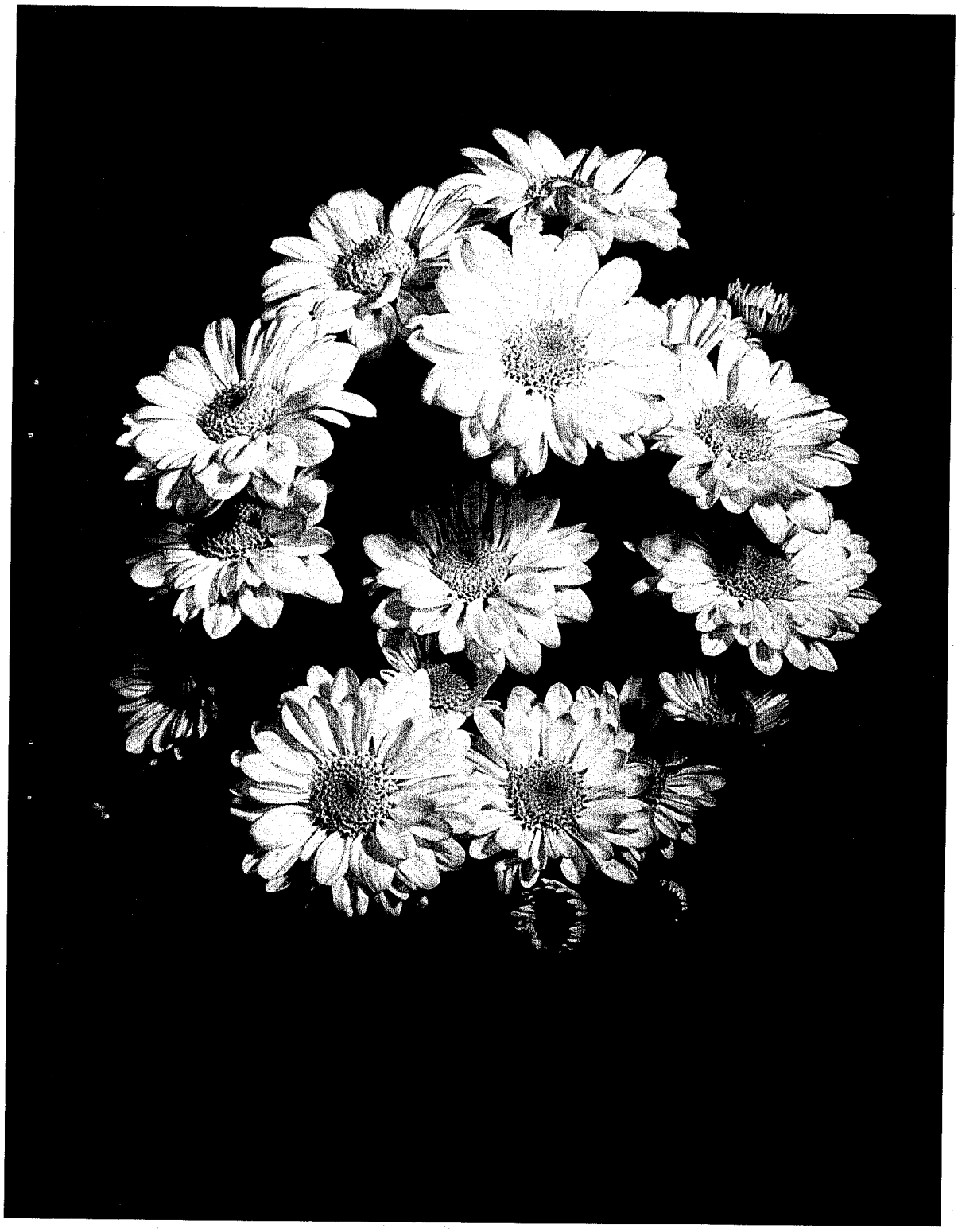

* * * * *